United States Patent
Kuusinen et al.

(10) Patent No.: US 8,102,839 B2
(45) Date of Patent: Jan. 24, 2012

(54) SYSTEM, APPARATUS, AND METHOD FOR ESTABLISHING CIRCUIT-SWITCHED COMMUNICATIONS VIA PACKET-SWITCHED NETWORK SIGNALING

(75) Inventors: Jarmo Kuusinen, Jyväskylä (FI); Matti Turunen, Tampere (FI); Jari Mutikainen, Helsinki (FI)

(73) Assignee: Nokia Corporation, Espoo (FI)

( * ) Notice: Subject to any disclaimer, the term of this patent is extended or adjusted under 35 U.S.C. 154(b) by 998 days.

(21) Appl. No.: 12/070,873

(22) Filed: Feb. 21, 2008

(65) Prior Publication Data

US 2008/0159276 A1    Jul. 3, 2008

Related U.S. Application Data

(63) Continuation of application No. 10/688,203, filed on Oct. 17, 2003, now Pat. No. 7,359,373.

(51) Int. Cl.
  *H04L 12/66* (2006.01)
  *H04L 12/28* (2006.01)
  *H04J 3/24* (2006.01)
  *H04J 3/16* (2006.01)

(52) U.S. Cl. ......... 370/352; 370/389; 370/466; 370/474

(58) Field of Classification Search .................. None
  See application file for complete search history.

(56) References Cited

U.S. PATENT DOCUMENTS

| | | |
|---|---|---|
| 6,519,568 B1 | 2/2003 | Harvey et al. |
| 6,757,533 B2 | 6/2004 | Lampela et al. |
| 7,746,849 B2 * | 6/2010 | Bodin et al. .............. 370/355 |
| 2002/0172338 A1 | 11/2002 | Lee et al. |
| 2002/0196775 A1 | 12/2002 | Tuohino et al. |
| 2003/0026245 A1 | 2/2003 | Ejzak |
| 2003/0035401 A1 | 2/2003 | Shaheen et al. |
| 2003/0156578 A1 | 8/2003 | Bergenlid et al. |
| 2004/0120505 A1 | 6/2004 | Kotzin et al. |
| 2004/0252674 A1 | 12/2004 | Soininen et al. |
| 2005/0025047 A1 | 2/2005 | Bodin et al. |
| 2005/0083909 A1 | 4/2005 | Kuusinen et al. |

FOREIGN PATENT DOCUMENTS

| | | |
|---|---|---|
| EP | 1 505 814 | 2/2005 |
| JP | 2001517910 | 10/2001 |
| JP | 2004088532 | 3/2004 |

(Continued)

OTHER PUBLICATIONS

Notice of Allowance dated Nov. 15, 2007 from U.S. Appl. No. 10/688,203, 6 pages.

(Continued)

*Primary Examiner* — Nittaya Juntima
(74) *Attorney, Agent, or Firm* — Hollingsworth & Funk, LLC

(57) ABSTRACT

A system, apparatus and method for establishing circuit-switched (CS) communications in packet-switched (PS) multimedia networks such as IMS, and providing services via the PS networks to CS domain users. A dialog is established between terminals through the PS multimedia network. A service is provided to at least one of the terminals by way of the dialog. CS bearer information, including an indication that a communication flow is requested via a CS network, is communicated between the terminals by way of the dialog. A communication flow via the CS network is effected between the terminals as directed by the CS bearer information. IMS or other PS multimedia network services can thus be provided to users otherwise communicating via the CS-domain.

17 Claims, 7 Drawing Sheets

FOREIGN PATENT DOCUMENTS

| WO | WO 03/003767 | 1/2003 |
|---|---|---|
| WO | WO03085904 | 10/2003 |
| WO | WO2004073279 | 8/2004 |
| WO | WO2004012415 | 12/2004 |

OTHER PUBLICATIONS

Office Action Response dated Oct. 30, 2007 from U.S. Appl. No. 10/688,203, 10 pages.
Office Action dated Sep. 14, 2007 from U.S. Appl. No. 10/688,203, 6 pages.
Office Action Response dated Aug. 2, 2007 from U.S. Appl. No. 10/688,203, 15 pages.
Office Action dated May 4, 2007 from U.S. Appl. No. 10/688,203, 17 pages.
Office Action Response dated Feb. 8, 2007 from U.S. Appl. No. 10/688,203, 13 pages.
Office Action dated Aug. 7, 2006 from U.S. Appl. No. 10/688,203, 19 pages.
Office Action Response dated May 31, 2006 from U.S. Appl. No. 10/688,203, 14 pages.
Office Action dated May 15, 2006 from U.S. Appl. No. 10/688,203, 3 pages.
Office Action Response dated Apr. 27, 2006 from U.S. Appl. No. 10/688,203, 14 pages.
Office Action dated Jan. 30, 2006 from U.S. Appl. No. 10/688,203, 12 pages.
Office Action Response dated Dec. 5, 2005 from U.S. Appl. No. 10/688,203, 13 pages.
Office Action dated Oct. 4, 2005 from U.S. Appl. No. 10/688,203, 12 pages.
Office Action Response dated Jul. 21, 2005 from U.S. Appl. No. 10/688,203, 16 pages.
Office Action dated Feb. 16, 2005 from U.S. Appl. No. 10/688,203, 11 pages.
Office Action dated Nov. 10, 2009 from U.S. Appl. No. 11/439,883, 27 pages.
International Preliminary Report on Patentability dated May 24, 2007 from PCT Application No. PCT/IB2004/002831, 5 pages.
International Search Report and Written Opinion dated May 22, 2005 from PCT Application No. PCT/IB2004/002831, 8 pages.
Office Action dated Jul. 20, 2010 from European Application No. 04769240.5, 6 pages.
Office Action dated Oct. 28, 2008 from Japanese Application No. 2006-534844, 6 pages.
Office Action dated Jun. 9, 2009 from Japanese Application No. 2006-534844, 6 pages.
3GPP TS 22..228 V6.4.0 (Sep. 2003). 3rd Generation Partnership Project; Technical Specification Group Services and System Aspects; Service requirements for the Internet Protocol (IP) multimedia core network subsystem; Stage 1 (Release 6). pp. 1-17.
3GPP TS 23..228 V6.2.0 (Jun. 2003). 3rd Generation Partnership Project; Technical Specification Group Services and System Aspects; IP Multimedia Subsystem (IMS); Stage 2 (Release 6). pp. 1-143.
Handley et al., SDP Session Description Protocol, RFC2327, Apr. 1998, pp. 1-42.

* cited by examiner

SYSTEM, APPARATUS, AND METHOD FOR ESTABLISHING CIRCUIT-SWITCHED COMMUNICATIONS VIA PACKET-SWITCHED NETWORK SIGNALING

CROSS-REFERENCE TO RELATED APPLICATIONS

This is a continuation application of application Ser. No. 10/688,203, filed Oct. 17, 2003, now issued as U.S. Pat. No. 7,359,373, the contents of which is incorporated herein by reference in its entirety.

FIELD OF THE INVENTION

This invention relates in general to network communications, and more particularly to a system, apparatus and method for establishing circuit-switched communications using signaling in packet-switched networks. In this manner, services provided via the packet-switched network can be provided to circuit-switched communication users.

BACKGROUND OF THE INVENTION

Advances in communication infrastructures and protocols have allowed standard computing devices to become valuable communication tools. Computers communicate with each other, and with other electronic devices, over networks ranging from local area networks (LANs) to wide reaching global area networks (GANs) such as the Internet. Other electronic devices have experienced similar transformations, such as mobile phones, personal digital assistants (PDAs), and the like. Today, these wireless devices are being used for a variety of different types of communication. For example, while the analog mobile phone was traditionally used for analog voice communications, the present-day mobile phone is a powerful communication tool capable of communicating voice, data, images, video, and other multimedia content. PDAs, once the portable calendaring and organizational tool, now often include network communication capabilities such as e-mail, Internet access, etc. With the integration of wireless and landline network infrastructures, information of all types can be conveniently communicated between wireless and landline terminals.

Network architectures exist that facilitate real-time services in operator networks for such terminals. For example, the 3rd Generation Partnership Project (3GPP) IP Multimedia core network Subsystem (IMS) is an architecture for supporting multimedia services via a Session Initiation Protocol (SIP) infrastructure. 3GPP has standardized the Universal Mobile Telecommunications System (UMTS) in various phases, where Release 5 included a system where the packet-switched core network (PS-CN) dominates over circuit-switched, and further took responsibility of telephony services. Release 5 introduced a new core network into the UMTS architecture, namely the IMS core that supports both telephony and multimedia services. The IMS interacts both with the Public Switched Telephone Network (PSTN) and the Internet (or other such large-scale network) to provide various multimedia services to users. In IMS environments, proxies are identified as Call State Control Functions (CSCF), of which various types exist, including a proxy CSCF (P-CSCF), a serving CSCF (S-CSCF), and interrogating CSCF (I-CSCF). Generally, an S-CSCF performs and/or assists in performing a number of functions, including controlling session management functions for the IMS, providing access to home network servers such as location services, authentication, etc. A P-CSCF generally serves as the point of contact for applications (such as the mobile terminal client applications), and performs and/or assists in performing functions such as translation, security, authorization, etc. An I-CSCF generally serves as a point of contact in the home network for connections destined to a subscriber of that home network or roaming subscribers currently located within that network's service area. It may perform a number of functions, such as assigning an S-CSCF to a user performing registration, contacting the Home Subscriber Server (HSS) to obtain the S-CSCF address, forwarding SIP requests/responses to the S-CSCF, etc.

The 3GPP IMS utilizes SIP in order to achieve a wide range of functionality with the network. SIP, defined by the Internet Engineering Task Force (IETF), is an end-to-end signaling protocol that facilitates (among other things) the establishment, handling and release of end-to-end multimedia sessions. It can be used in applications such as Internet conferencing, telephony, presence, events notification, instant messaging, and the like. SIP enables network endpoints or "User Agents" (UA) to discover one another and to agree on a session characterization. User agents (UA) refer to the network endpoints that initiate SIP requests to establish media sessions, and to transmit/receive information. In order to locate other users, SIP utilizes an infrastructure of network proxy servers such as the aforementioned CSCFs to which users can send registrations, invitations to sessions, and other requests via their terminals. SIP supports various aspects of establishing and terminating sessions, such as user availability, session setup such as ringing, session management, and some limited terminal capabilities.

For IMS communication, information transfer is based on the Internet Protocol (IP). The IP is designed for use in interconnected systems of packet-switched communication networks, such as the Internet. This network layer protocol divides messages into datagrams that are transmitted over the network to the receiving device by way of various network intermediaries, and reassembled at the receiving device. IP is a "connectionless" protocol, meaning there is no continuous connection between the endpoints of the communication. Instead, the packets are sent from the sender, where packets may take different paths, and network congestion may occur along any of the paths. The order in which packets are received may therefore be different from the order in which they are sent, and transmission latencies may cause real-time or streaming communications to be adversely affected.

For this reason, such real-time/streaming communication is often performed in the circuit-switched (CS) domain, as it has traditionally been done. CS networks are those in which a physical path is obtained for a single connection between endpoints, where this physical path is dedicated to the connection for its duration. Real-time and other streaming services (e.g., audio, video) have traditionally been provided via CS networks to preserve the time relation between endpoints of the communication. As described above, such services may now be provided via the packet-switched (PS) domain. For example, "voice over IP" (VoIP) generally refers to services for managing the delivery of voice information using IP, such that the voice data is sent via packets in the PS domain rather than the traditional CS domain. To address the possible network latency issues, VoIP uses the real-time protocol (RTP) to help towards the goal of delivering packets in a timely fashion.

However, many mobile stations (MS) and other terminals do not support RTP-based VoIP or other real-time and/or streaming services over IP. Complications in providing real-time IP services in mobile networks are primarily due to the demand that is placed on the network, where IP networks have often been based on a best-effort model. The requirement for high data transmission rates, as well as appropriate quality of service support to guarantee sufficient bit rates and other such requirements, are current impediments to ubiquitous real-time IP services. Furthermore, MSs may not currently or in the future support real-time and/or streaming services through a PS network using protocols other than IP. For example, a future PS network may use a network protocol different from IP, where certain legacy devices do not support packet-based communication using such a network protocol.

However, there may be services associated with such IP or other PS networks that may be desirable to such device users, but would be unavailable to such users. For example, IMS offers users a wide variety of different services. An MS that does not support VoIP or other similar services will need to conduct such communications in other ways, such as by way of circuit-switched telephony services. In such cases, the user will not be able to utilize the various IMS services that would otherwise be available if the MS was communicating via VoIP or other service through the IMS. Further, an operator's third generation (3G) network (or beyond) may provide VoIP and similar services, but may not provide all of the services available via the IMS network. In these cases, it would be desirable to offer the user the IMS services, while allowing other communication over the CS network, VoIP-enabled 3G network, etc.

Accordingly, there is a need in the communications industry for a manner of establishing circuit-switched communications using signaling in packet-switched networks. A further need exists for a manner for allowing users communicating via circuit-switched networks to gain the benefit of services provided in non-circuit-switched networks. The present invention fulfills these and other needs, and offers other advantages over the prior art.

SUMMARY OF THE INVENTION

To overcome limitations in the prior art described above, and to overcome other limitations that will become apparent upon reading and understanding the present specification, the present invention discloses a system, apparatus and method for establishing circuit-switched communications using signaling in packet-switched networks.

In accordance with one embodiment of a method of the invention, services are provided via a packet-switched (PS) multimedia network to users communicating in a circuit-switched (CS) domain. A dialog is established between terminals through the PS multimedia network. A service(s) is provided to at least one of the terminals by way of the dialog. CS bearer information, including an indication that a communication flow is requested via a CS network, is communicated between the terminals, also by way of the dialog. A communication flow via the CS network is effected between the terminals as directed by the CS bearer information.

According to more particular embodiments of such a method, establishing the dialog between the terminals through the PS multimedia network involves establishing the dialog between the terminals utilizing the Session Initiation Protocol (SIP) via the PS multimedia network. In another particular embodiment, the PS multimedia network includes an Internet Protocol Multimedia Subsystem (IMS), and establishing a dialog between a plurality of terminals involves establishing a dialog using the Session Initiation Protocol (SIP) through the IMS. In one embodiment, the dialog is established using a SIP INVITE request from one of the terminals to the other(s), where communicating CS bearer information may be effected by way of a session description provided via the SIP INVITE message body. In another embodiment, the session description is provided using the Session Description Protocol (SDP), where the CS bearer information is provided via SDP. The CS information may be carried by SDP by providing some or all of the CS information by way of, for example, a media type particular to communication flows via the CS network, an SDP connection data field identifying the CS network, a sub-field of a media type that is particular to communication flows via the CS network, an SDP attribute indicative of the type of communication flow to be performed via the CS network, a sub-field of an application media type that is particular to the communication flows via the CS network, and/or a session-level attribute indicating that the communication flow is to be effected via the CS network. In other embodiments, the CS bearer information is communicated by way of a CS-specific content type value associated with a SIP Content-Type header, or by way of a CS-specific value associated with a CS-specific SIP header.

The services provided may be any service available via the IMS or other PS multimedia network. For example, such services may include a multimedia version of Caller Line Identification service (referred to herein as multimedia CLI or MCLI), video service, audio service, video telephony and other streaming video services, multimedia conference service, voicemail, call forwarding, call transfer, or application sharing service. The CS-based communication may also take on various forms such as, for example, a real-time media transmission, a conversational quality of service class flow, a streaming quality of service class flow, a voice call, a video and/or audio transmission, a facsimile transmission, etc.

In accordance with another embodiment of the invention, a method is provided for establishing a circuit-switched (CS) connection between at least two terminals. A dialog is established between the terminals through a packet-switched (PS) multimedia network. CS bearer information is communicated between the terminals via the dialog, where the CS bearer information includes some an indication that a communication flow is requested via a CS network. A connection is established via the CS network, based at least in part on the CS bearer information provided by way of the dialog. The communication flow is effected between the terminals using the connection established by way of the CS network.

In accordance with another embodiment of the invention, a terminal is provided for receiving services via a packet-switched (PS) multimedia network and for communicating via a circuit-switched (CS) network. The terminal includes a processing system. A first user agent is operable by way of the processing system, and is configured to establish a dialog with at least one other targeted recipient terminal through the PS multimedia network, and to communicate CS bearer information to the targeted recipient terminal via the dialog, where the CS bearer information includes at least an indication that a communication flow is requested via a CS network. A second user agent operable via the processing system is configured to conduct the communication flow between the terminal and the targeted recipient terminal by way of the CS network as directed by the CS bearer information.

In more particular embodiments of such a terminal, the first user agent is configured to utilize at least one service provided via the PS multimedia network, which may be, for example, an IP Multimedia Subsystem (IMS). In other particular embodiments, the first user agent includes a Session Initiation Protocol (SIP) user agent, where the dialog is effected using SIP. In other particular embodiments, a session description user agent is operatively coupled to the SIP user agent, and is configured to provide the CS bearer information to be communicated by the SIP user agent. Such a session description user agent may be provided, for example, by a Session Description Protocol (SDP) user agent. Such an SDP user agent may be configured to provide the CS bearer information by way of, for example, a media type particular to communication flow via the CS network, a sub-field of a media type that is particular to communication flow via the CS network, a sub-field of an application media type that is particular to the communication flow via the CS network, and/or a session-level attribute indicating that the communication flow is to be effected via the CS network. In still other embodiments, the SIP user agent is configured to provide the CS bearer information, such as by way of a CS-specific content type value associated with a SIP Content-Type header, and/or a CS-specific value associated with a CS-specific SIP header. The terminal may be a landline terminal such as a desktop computer, workstation, or the like, or may be a wireless device such as a mobile phone, PDA, or other wireless device that can be coupled to the IMS system via some Radio Access Network (RAN).

In accordance with another embodiment of the invention, a system for providing IMS-based services to users communicating time delay-sensitive information over a circuit switched (CS) network is provided. Such time delay-sensitive information may include, for example, voice calls, video calls, facsimile transmissions or other conversational and/or streaming QoS class flows. The system includes at least a sender terminal and a receiver terminal. The sender terminal includes a processing system, and a SIP user agent configured to initiate a dialog with the receiver terminal through the IMS, and to communicate CS bearer information to the receiver terminal via the dialog. The sender terminal also includes a CS communication user agent configured to effect the communication flow with the receiver terminal via the CS network as directed by the CS bearer information. The receiver terminal includes a processing system, and a SIP user agent configured to recognize the CS bearer information, and to respond to the sender terminal acknowledging receipt of the CS bearer information. The receiver terminal further includes a CS communication user agent configured to effect the communication flow with the sender terminal via the CS network as directed by the CS bearer information.

According to another embodiment of the invention, a computer-readable medium is provided, which has instructions stored thereon that are executable by a computer system for establishing a circuit-switched (CS) connection between at least two terminals. The instructions perform steps including establishing a dialog between the at least two terminals through a packet-switched (PS) multimedia network, communicating CS bearer information between the at least two terminals via the dialog, where the CS bearer information includes at least an indication that a communication flow is requested via a CS network, establishing a connection via the CS network based at least in part on the CS bearer information provided via the dialog, and effecting the communication flow between the at least two terminals using the connection established via the CS network.

These and various other advantages and features of novelty which characterize the invention are pointed out with particularity in the claims annexed hereto and form a part hereof. However, for a better understanding of the invention, its advantages, and the objects obtained by its use, reference should be made to the drawings which form a further part hereof, and to accompanying descriptive matter, in which there are illustrated and described specific examples of a system, apparatus, and method in accordance with the invention.

BRIEF DESCRIPTION OF THE DRAWINGS

The invention is described in connection with the embodiments illustrated in the following diagrams.

DETAILED DESCRIPTION OF THE INVENTION

Figure 1:
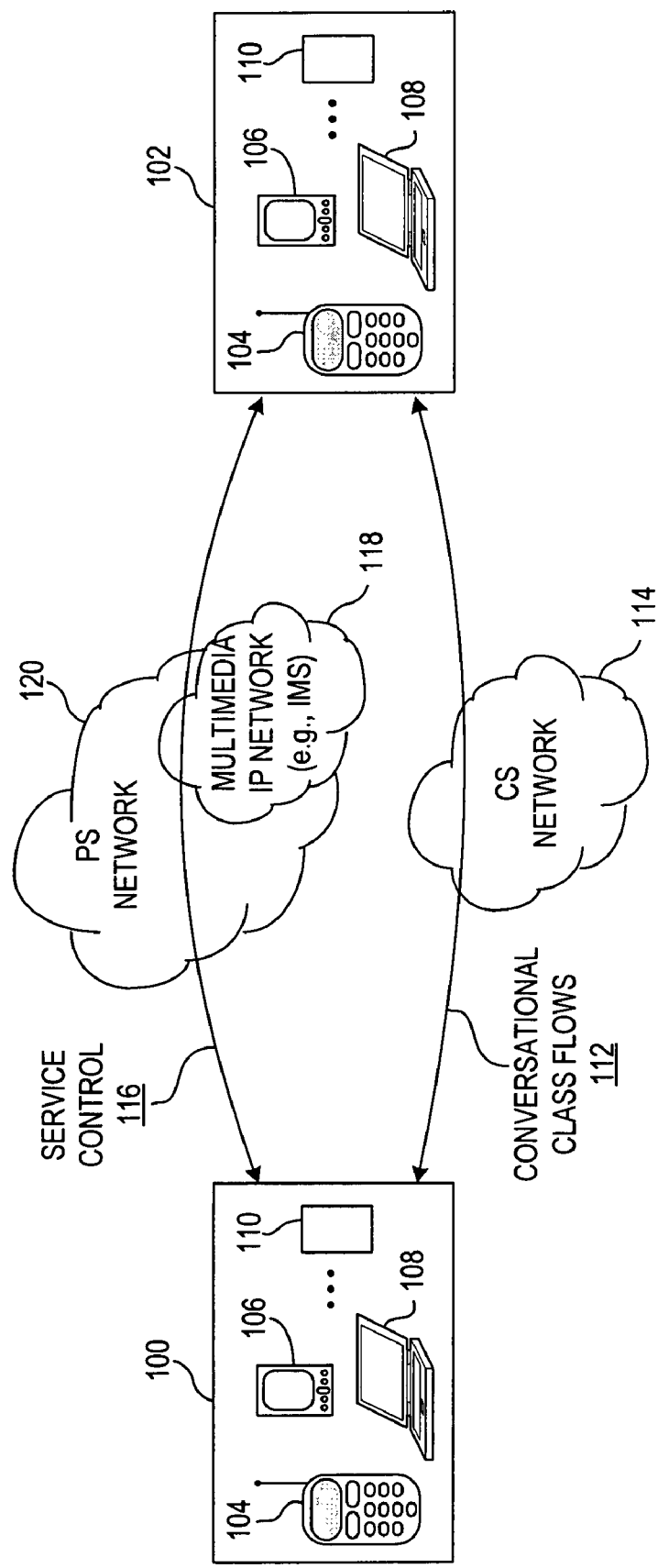
FIG. 1 is a block diagram generally illustrating the ability for users without VoIP or other IP-based real-time/streaming communication capability to utilize IMS services in accordance with one embodiment of the present invention.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

In the following description of various exemplary embodiments, reference is made to the accompanying drawings which form a part hereof, and in which is shown by way of illustration various embodiments in which the invention may be practiced. It is to be understood that other embodiments may be utilized, as structural and operational changes may be made without departing from the scope of the present invention.

Generally, the present invention provides a manner for establishing circuit-switched (CS) communications using signaling in packet-switched (PS) networks. A user can establish a dialog with another user over a PS multimedia network, such as IMS, via a signaling protocol. By communicating over the PS multimedia network, services that are provided by that PS multimedia network are available to one or both users. However, other communication can occur between the users by way of one or more CS networks, where the dialog established via the PS multimedia network includes information relevant to the CS network communications. For example, a user who has no VoIP capability can establish a dialog via the PS multimedia network, utilize services made available by that PS multimedia network, and conduct telephony or other communications requiring real-time conversational interaction via the CS network.

For Internet Protocol Multimedia Subsystem (IMS) communication, information transfer is based on the Internet Protocol (IP) which is designed for use in interconnected systems of packet-switched communication networks, such as the Internet. This network layer protocol divides messages into packets or "datagrams" (used interchangeably herein) which includes both the sender's and receiver's unique network address. The packets are transmitted over the network to the receiving device by way of various network intermediaries, and reassembled at the receiving device (e.g., using the Transmission Control Protocol, User Datagram Protocol, etc.). IP is a "connectionless" protocol, meaning there is no continuous connection between the endpoints of the communication. Instead, the packets are sent from the sender, where packets may take different paths, and network congestion may occur along any of the paths. The order in which packets are received may therefore be different from the order in which they are sent, and transmission latencies may cause real-time or streaming communications to be adversely affected.

Due to the potential for such latencies, real-time/streaming communication is often performed in the CS domain. Real-time services such as telephony and streaming services have traditionally been provided via CS networks to preserve the time relation between endpoints of the communication. As previously indicated, such services such as VoIP have recently entered the packet-switched (PS) domain. To address the possible network latency issues, VoIP uses the real-time protocol (RTP) to help towards the goal of delivering packets in a timely fashion. However, many mobile stations (MS) and other terminals do not support RTP-based VoIP or other real-time and/or streaming services over IP. Furthermore, MSs may not currently or in the future support real-time and/or streaming services through a PS network (e.g., IMS) using protocols other than IP. However, services made available via such network such as IMS may be desirable to such users, who would otherwise not be able to utilize such services without the benefit of the present invention. An MS that does not support VoIP or other similar services will need to conduct such communications in other ways, such as by way of circuit-switched telephony services. In such cases, the user will not be able to utilize the various IMS services that would otherwise be available if the MS was communicating via VoIP or other service through the IMS. Further, an operator's third generation (3G) network (or beyond) may provide VoIP and similar services, but may not provide all of the services available via the IMS network. In these cases, it would be desirable to offer the user the IMS services, while allowing other communication over the CS network, VoIP-enabled 3G network, etc.

The present invention allows IMS services to be offered to users in the CS domain or other network domains that would otherwise not use the IMS. Therefore, the IMS services can be offered for users even if the operator's 3G network already has VoIP (or analogous) capabilities, or if the MS does not support such VoIP or analogous services, or other scenario where the IMS would not otherwise be involved. It should be noted that while various embodiments of the invention set forth herein are described in terms of IMS, it will be apparent to those skilled in the art from the description provided herein that the invention is applicable to other analogous situations where a network subsystem facilitates communication via particular protocol to which certain MSs do not support, or where the MS may simply benefit from using services from such a network subsystem. Thus, the present invention is equally applicable to network subsystems (e.g., PS multimedia networks) other than IMS. For example, the present invention is applicable to other infrastructures supporting the signaling protocol employed to establish the PS session. In a more particular example where SIP is used as the signaling protocol to establish the PS session, the present invention is applicable to any operator/service provider-operated SIP infrastructure. IMS represents one such SIP infrastructure.

FIG. 1 is a block diagram generally illustrating the ability for users without VoIP or other IP-based real-time/streaming communication capability to utilize IMS services in accordance with one embodiment of the present invention. The illustrated embodiment of FIG. 1 involves communication between two mobile devices 100, 102, although the invention is equally applicable to landline terminals such as desktop computers, workstations, etc. The invention is also equally applicable to communications involving an application server or other network entity providing the users with particular services (e.g., conferencing server, etc.). Therefore, while various embodiments described herein are described in connection with communication between mobile devices, it should be recognized that the present invention is applicable to communications involving other mobile or landline terminals. In the illustrated embodiment of FIG. 1, the mobile devices 100, 102 may include devices such as mobile phones 104, Personal Digital Assistants (PDAs) 106, portable computers 108, or other devices capable of accessing networks via wireless communication.

In accordance with the present invention, IMS services requiring a substantial preservation of time relationship between communication endpoints 100, 102 are provided to the users using CS domain bearers to carry the real-time/streaming media, such as a voice call. For example, conversational QoS class flows 112 such as voice calls are carried in the CS domain as represented by the CS network 114. Other class flows that are sensitive to the time relationship between communication endpoints may also be carried through the CS network 114, such as the streaming QoS class which includes applications such as streaming video, audio, etc. Although such communication is conducted through the CS domain, the present invention allows IMS services to be provided to the users of devices 100, 102 by performing service control 116 through the IMS or other similar multimedia IP network 118 associated with a PS network 120. For example, the Session Initiation Protocol (SIP) is used for establishing, modifying, and terminating sessions through IMS 118, and service control is performed using SIP through the IMS 118 in one embodiment of the invention. The IMS services available to the users may include, for example, multimedia Caller Line Identification (MCLI), streaming video and audio services, multimedia conferences, application sharing, voicemail, call forwarding, call transfer, and the like. In accordance with the invention, users 100, 102 who do not otherwise want to, or have the capability to communicate conversational, streaming, or other time-sensitive class flows via the PS network 120 and multimedia IP network 118 can communicate such class flows via the CS network 114, while still receiving one or more services via the multimedia IP network (e.g., IMS) 118.

In accordance with one embodiment, the CS session 112 through the CS network 114 and dialog 116 through the multimedia IP network 118 are tied together in the terminal. For example, in the IMS context, the CS session 112 and SIP dialog 116 are tied together in the terminals 100, 102 using a particular session description definition. There is no need to make changes or additions to the network, as the operator can configure the IMS elements to support the functionality. However, SIP messages carrying CS-specific session descriptions should not be blocked by the Call Session Control Function (CSCF) in the IMS domain, which is an operator policy decision.

In one embodiment of the invention, a session description is extended or otherwise modified to carry CS-specific information between the endpoints 100, 102 in connection with a session setup. For example, in a SIP session setup, the CS-specific information may be carried using the Session Description Protocol (SDP). The session description includes an indication from the terminal (e.g., MS 100), that the CS domain will be used for the conversational, streaming, or other delay-sensitive class flow. The routing number may be carried in the response (e.g., SIP response) to the request. Such a routing number may be used, for example, in conferencing or in multiparty peer-to-peer communications to obtain the dynamic conference number from the server to the initiating terminal.

When the SIP dialog setup is complete or is otherwise in an appropriate session progress state, the initiator such as MS-A 100 uses MS-Bs number to initiate the CS call. The MSs are therefore configured to the SIP dialog and corresponding CS bearer, where the MSs are configured to operate with technologies that carry multiple services at the same time. For example, Dynamic synchronous Transfer Mode (DTM) may be used, which is a synchronous transport network technology able to carry multiple services at different data rates at the same time. DTM is a form of circuit switching for networks that employs Time Division Multiplexing (TDM) in a way that dynamically reallocates available bandwidth to users that need it. As another example, Wideband Code Division Multiple Access (WCDMA) multiple Radio Access Bearers (RAB), referred to as Multi-RAB, provides for the ability to allow an MS to use two RABs simultaneously. These or other analogous current or future technologies may be used to support the concurrent service control 116 and conversational/streaming flows 112 in accordance with the present invention.

As alluded to above, MS-A 100 may initiate the CS call when the SIP dialog setup is complete, or before SIP dialog setup completion. For example, one embodiment involves initiating the CS call by the MS-A 100 upon receipt of an acknowledgment from MS-B 102 indicating completion of a successful dialog setup (e.g., 200/OK response). In other embodiments, the CS call may be initiated before the dialog is completely negotiated. This may allow for a reduction in the collective setup time, and in some instances may allow for different user experiences in some applications. For example, MS-A 100 may initiate the CS call (e.g., send the SETUP) when it receives a provisional response such as a session progress message (e.g., SIP 183 response).

Further, the MSs 100, 102 register with the multimedia IP network 118 to facilitate the service control 116. For example, the MSs 100, 102 may register with the IMS using a SIP REGISTER message. In a more particular example, a SIP REGISTER message may be sent to the nearest Proxy Call Session Control Function (P-CSCF) for that user, where the nearest P-CSCF may be located using Domain Name Service (DNS) SRV, Dynamic Host Configuration Protocol (DHCP), or the like. If the P-CSCF is in a visited network, the P-CSCF locates the Interrogating CSCF (I-CSCF) of the home network for the user, and sends a REGISTER message to the Serving (S-CSCF). Once registered, the MS can be located for communication. It should be noted that IMS roaming is supported between visited and home networks, where the P-CSCF is located in the visited network. This, however, is not a requirement, as other roaming support such as GPRS roaming support is enough, and the P-CSCF can be located in the home network.

Figure 2:
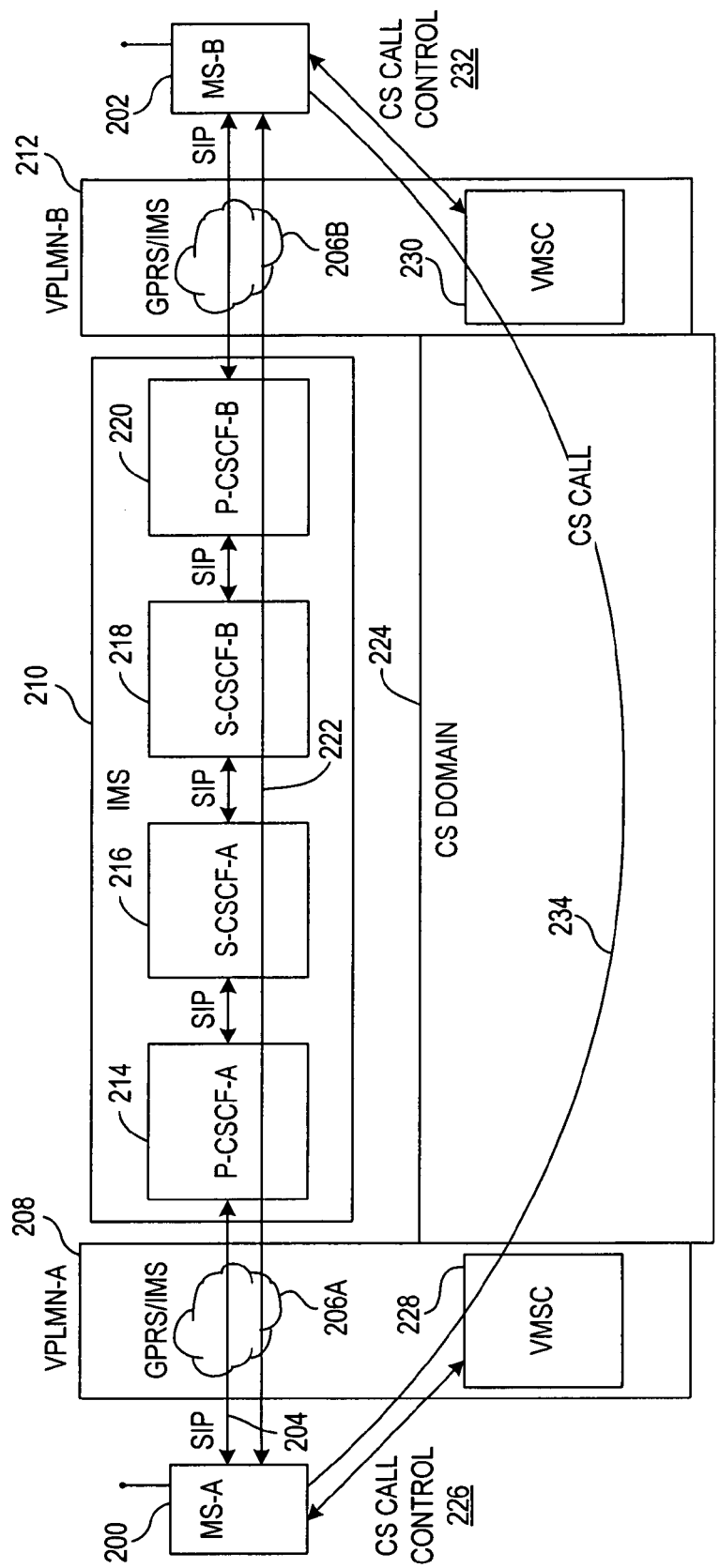
FIG. 2 is a block diagram illustrating one embodiment for establishing CS sessions via IMS in accordance with the present invention.

Referring now to FIG. 2, a block diagram illustrating one embodiment for establishing CS sessions via IMS in accordance with the present invention. This embodiment again assumes communication between two wireless devices, labeled MS-A 200 and MS-B 202. MS-A 200 initiates a SIP dialog 204 through the GPRS/IMS network 206A at the Visited Public Land Mobile Network (VPLMN) 208. The SIP dialog 204 is established through the IMS domain 210 to MS-B 202 via the GPRS/IMS 206B associated with the VPLMN-B 212 associated with MS-B 202. More particularly, MS-A 200 sends a SIP request, such as a SIP INVITE request, to the P-CSCF-A 214 associated with the VPLMN-A 208. The INVITE is routed through S-CSCF-A 216, which in turn routes the request through the S-CSCF-B 218 and P-CSCF-B 220 associated with VPLMN-B 212. The SIP INVITE request has a message body that includes the session description that carries CS-specific information, including a CS bearer media description, in accordance with the present invention. Such a session description is described in greater detail below. In this manner, a SIP dialog 222 is established between MS-A 200 and MS-B 202 via the IMS.

MS-B 202 will parse the CS-specific information from the INVITE request, and MS-B 202 will thus become aware that MS-A 200 wants to conduct a CS-based communication. Other IMS services may be used, such as multimedia Caller Line Identification (MCLI), where MS-B 202 may be presented with a photo or other image of the caller, a corporate logo, vCard, other graphics, audio clip, or the like. When MS-B 202 responds to the INVITE, the session description of MS-B 202 is provided to MS-A 200, where the session description also provides the CS bearer media description.

When the SIP dialog 222 has been established and the session descriptions have been exchanged, MS-A 200 starts a call setup procedure through the CS domain 224 using MS-B's 202 number, as depicted by the CS call control 226. For example, in a Global System for Mobile communication (GSM) network, call establishment determines the locally responsible switch, which is the Visited Mobile Switching Center (VMSC) 228 in the illustrated embodiment. The VMSC 228 signals to the Visiting Location Register (VLR; not shown) that the MS-A 200 identified by the temporary TMSI in the location area LAI has requested service access. After authentication and other procedures, the connection request is signaled to the remote VMSC 230, and CS call control 232 occurs with MS-B 202. MS-B 202 will be expecting a CS call, due to the SIP dialog 222 previously established that indicated so. In this manner, the CS call 234 is established.

Figure 3:
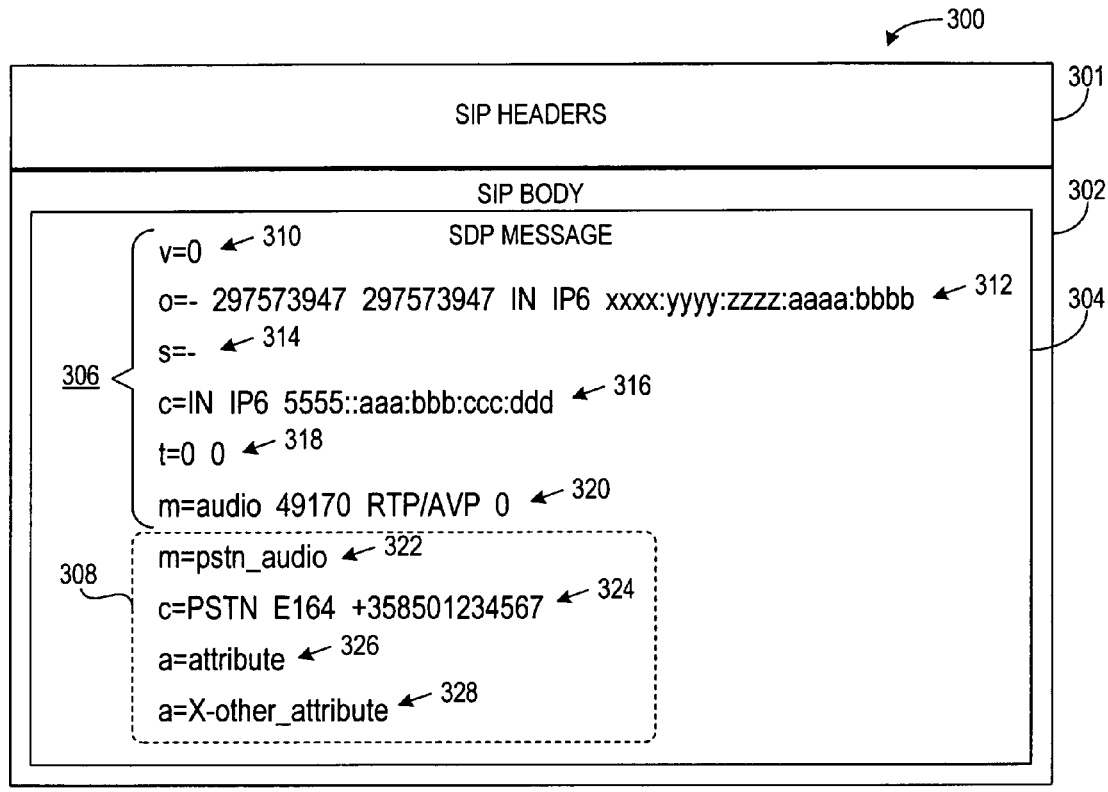
FIG. 3 is a diagram illustrating a representative manner for performing service control using SIP through IMS in accordance with one embodiment of the invention.

As previously indicated, the session through IMS may be established using SIP. FIG. 3 is a diagram illustrating a representative manner for performing service control using SIP through IMS in accordance with one embodiment of the invention. The syntax for a SIP message 300 generally includes at least a message header 301 and a message body 302. The message header 301 includes fields such as a "Via" field to identify an address to which responses are expected; a "To" and "From" field to identify the targeted recipient and sender respectively; a "Call-ID" representing a unique identifier for the call; content length and type, and the like.

The details of the session, media type, codec, sampling rate, and/or other details are not described using SIP. Instead, the message body 302 of a SIP message includes a description of the session, encoded in some other protocol format, such as the Session Description Protocol (SDP). SDP may be used for describing multimedia sessions for the purposes of session announcement, session invitation, and other forms of multimedia session initiation. Other protocol formats may also be used to provide such a session description via the body of the SIP message, and any well-defined format for conveying sufficient information to participate in a multimedia session may be used in accordance with the present invention. SDP is assumed in the embodiments of FIGS. 3-6, and represents just one manner in which such session description details may be provided in accordance with the present invention. Thus, in the illustrated embodiment of FIG. 3, the message body 302 includes an SDP message 304 as at least a part of the SIP message body 302. The SDP message 304 is carried by the SIP message analogously to the manner in which a web page is carried via an HTTP message.

In the example of FIG. 3, the SDP message 304 includes a representative example of a common portion 306 of an SDP message. The message lines of this portion 306 illustrate representative description information that may be associated with a typical SDP message. A session description includes a session-level description such that the description may apply to the entire session and all media streams. SDP structure generally involves a session-level section followed by zero or more media-level sections. The session-level part starts with a "v" line 310 relating to the protocol version, and continues to the first media-level section that starts with an "m" line relating to the media name. The media-level section continues to the end of the session description, or to the next media description. For example, in the illustrated embodiment, one media-level section starts at line 320, and another at line 322. In general, session-level values are the default for all media unless overridden by an equivalent media-level value.

As is known in the art, other session descriptor items are included in the SDP message portion 306. For example, the "o" field 312 may indicate the originator of the session ("–" in the illustrated example, indicating the originating device does not support or otherwise include a user name), plus a session ID, session version number (e.g., IN IP6), etc. The "s" field 314 represents the session name. The "c" field 316 represents the connection data, which in the illustrated embodiment represents session-level connection data. It includes the network type (IN) and address type (IP6), and a connection address (e.g., 5555::aaa:bbb:ccc:ddd:). The "t" field 318 represents the time that the session is active for conferences (start/stop times "0 0" in the illustrated embodiment). The "m" field 320 represents the media description, which includes several sub-fields including the media type (e.g., audio), transport port to which the media stream will be sent (e.g., 49170), transport protocol (e.g., RTP/AVP which is the Real-time Transport Protocol using the Audio/Video profile), and media format (e.g., 0).

In accordance with one embodiment of the invention, an SDP extension 308 is provided, which represents additional SDP message lines that may be included to communicate the CS-specific information for indicating that a CS connection will be used. In this example, the SDP extension provides for a new media type. More particularly, the SDP extension 308 includes a media description 322, which includes a new media type "pstn_audio." In accordance with the invention, various new media types are provided to identify the CS bearer and associated media type. For example, the new media type "pstn_audio" represents an audio media type for the CS bearer. Similarly, new media types such as "pstn_video," "pstn_fax," and so forth can be provided for video, fax, and other media types for the CS bearer. Such new media types may be registered, such as by registration with Internet Assigned Numbers Authority (IANA). In some embodiments, the media description 322 may also carry additional information regarding the media, such as audio/video codecs, and the like.

The representative SDP extension 308 of FIG. 3 also includes a connection data field 324. The network type "PSTN" describes the connection parameters for PSTN calls, including the phone number (e.g., +358501234567) of the sender of the SDP. Other network types for CS networks may be alternatively provided. A phone number format (e.g., E164) may be provided as well.

Attributes may be provided, as shown on SDP extension lines 326, 328. Attribute fields may be of different forms. A property attribute is of the form "a=<flag>". These are binary attributes, and the presence of such an attribute indicates that the attribute is a property of the session. A value attribute is of the form "a=<attribute>:<value>", where the <value> defines a characteristic of the <attribute>. In the illustrated embodiment, a property attribute such as shown in extension line 326 may optionally be provided to add more information about the media, where "attribute" is any desired registered attribute. Similarly, the x-extension line 328 may optionally be used to identify unregistered attributes.

It is noted that the same SDP 304 can include a definition for both CS (e.g., PSTN) and IP sessions. For example, the media description illustrated at line 320 can be used for IP sessions, and the media description illustrated at line 322 of the SDP extension 308 may be used for PSTN communications.

Figure 4:
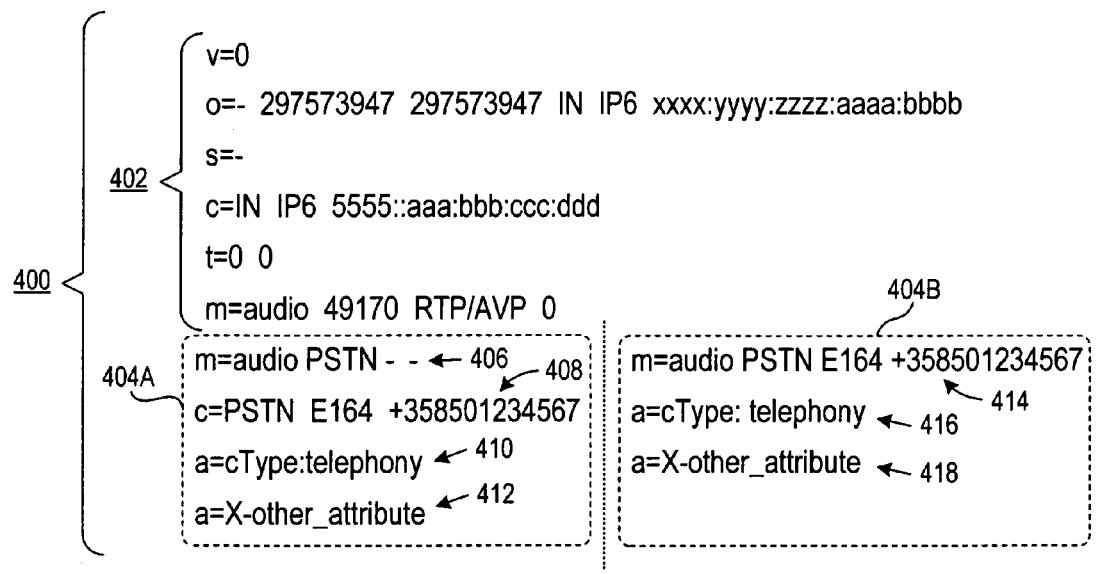
FIG. 4 is a diagram illustrating another embodiment of an SDP extension in accordance with the present invention, where a new sub-field is provided to the media type.

FIG. 4 is a diagram illustrating another embodiment of an SDP extension in accordance with the present invention, where a new sub-field is provided to the media type. The SDP message 400 includes a first SDP message portion 402, and SDP extensions 404A, 404B in accordance with alternative embodiments of the present invention. SDP extensions 404A and 404B illustrate alternative, representative SDP extensions where a new sub-field to the media type is provided in accordance with the present invention.

The first SDP message portion 402 is analogous to the SDP message portion 306 described in connection with FIG. 3, and is not further described here. A first representative SDP extension 404A includes a media description 406, that includes an existing media type, such as audio, video, etc. In the illustrated embodiment, the media description 406 includes the known media type "audio." The media description 406 of the SDP description 400 includes a new sub-field type to the media type in accordance with the illustrated embodiment of the invention. One such new sub-field type in the media description 406 is a "PSTN" sub-field type, representing the Public Switched Telephone Network (PSTN). This sub-field type indicates that the media type, audio, will be communicated via a CS bearer which is the PSTN in the illustrated example. The new sub-field type "PSTN" may be introduced to add the PSTN call information. Other sub-field types for different CS bearers may be designated as media sub-field types in accordance with the embodiment described in connection with FIG. 4.

The connection data field 408 also includes a new sub-field type, which is "PSTN" in the illustrated SDP extension 404A. Such a new sub-field type describes the connection parameters for PSTN calls, including, for example, the phone number (e.g., +358501234567) of the sender of the SDP message 400, and the phone number format (e.g., E164) if necessary. The type of service may be identified, such as audio, video, fax, and the like. An attribute field 410 may be used to identify a new attribute to indicate the connection type. The new attribute type is shown in SDP extension 404A as "cType," which corresponds to a new connection attribute, and the attribute value is "telephony." The new attribute type may be used to identify any desired connection attributes for the CS bearer, such as "a=cType:telephony," "a=cType:video_telephony," "a=cType:fax," or the like. Further, other attributes may be provided, whether registered or not. For example, the representative SDP extension 404A includes an x-extension line 412 to optionally identify unregistered attributes, shown as "X-other-attribute."

It is noted that the connection data field 408 may be omitted, if all the necessary parameters are added on the media description line. Such an embodiment is illustrated by SDP extension 404B, where the media description 414 includes an audio type, and a new sub-field type PSTN, as well as the phone number (e.g., +358501234567) of the sender of the SDP message 400, and the phone number format (e.g., E164) if necessary. Again the new connection type "cType" may be identified as shown at attribute field 416, and other attributes such as shown at x-extension line 418 may optionally be used to identify unregistered attributes.

Figure 5:
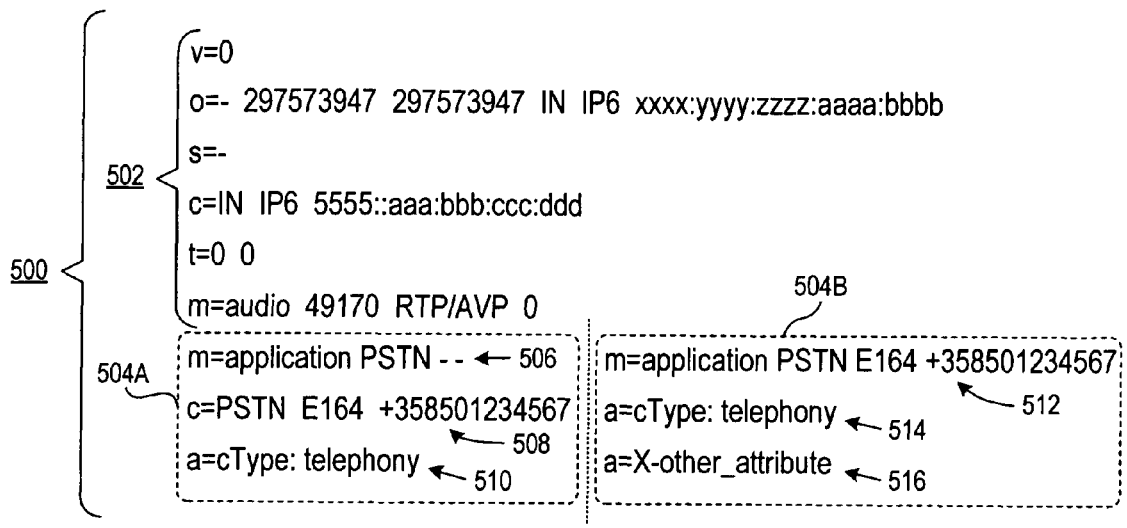
FIG. 5 is a diagram illustrating another embodiment of an SDP extension in accordance with the present invention, where an application media type is implemented.

FIG. 5 is a diagram illustrating another embodiment of an SDP extension in accordance with the present invention, where an application media type is implemented. The SDP message 500 includes a first SDP message portion 502, and SDP extensions 504A, 504B in accordance with alternative embodiments of the present invention. SDP extensions 504A and 504B illustrate alternative, representative SDP extensions where a new application media type is provided in accordance with the present invention.

The first SDP message portion 502 is analogous to the SDP message portion 306 described in connection with FIG. 3, and is not further described here. A first representative SDP extension 504A includes a media description 506, using a standard "application" media type, with a new subtype "PSTN," inserted to define a PSTN call. Other analogous subtypes identifying CS bearers may alternatively be used in such an embodiment. If desired or necessary, the media description 506 may also carry additional information regarding the media, such as audio/video codecs, etc.

The connection data field 508 describes the connection parameters for PSTN calls in the illustrated embodiment. The connection parameters may include, for example, the phone number (e.g., +358501234567) of the sender of the SDP, and the phone number format (e.g., E164) if necessary. The type of service may be identified, such as audio, video, fax, and the like. An attribute field 510 may be used to identify a new attribute to indicate the connection type. The new attribute type is shown in SDP extension 504A as "cType," which corresponds to a new connection attribute, and the attribute value is "telephony." The new attribute type may be used to identify any desired connection attributes for the CS bearer, such as "a=cType:telephony," "a=cType:video_telephony," "a=cType:fax," or the like. Further, other attributes may be provided, whether or not such attributes are registered, by using the appropriate attribute or x-attribute.

It is noted that the connection data field 508 may be omitted, if all the necessary parameters are added on the media description line. Such an embodiment is illustrated by SDP extension 504B, where the media description 512 includes the "application" type and new subtype "PSTN" as previously described, and also includes connection parameters. The connection parameters may include, for example, the phone number (e.g., +358501234567) of the sender of the SDP, and the phone number format (e.g., E164) if necessary. Attributes may again be provided via the new connection type "cType," as shown at attribute field 514, and other attributes such as shown at x-extension line 516 may optionally be used to identify unregistered attributes.

Figure 6:
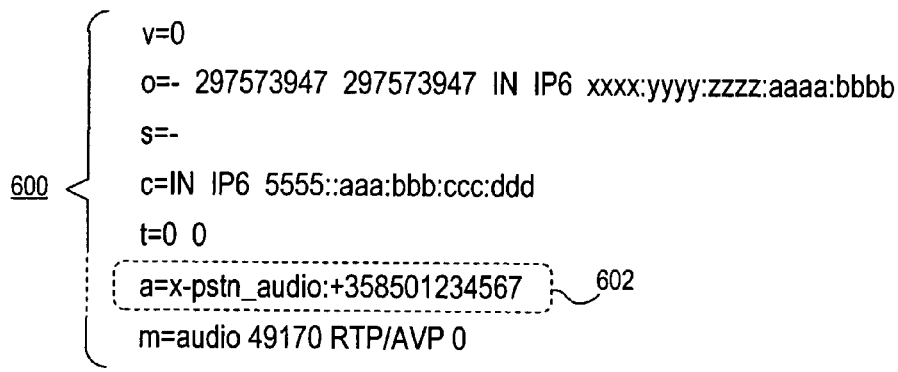
FIG. 6 is a diagram illustrating another embodiment of an SDP extension in accordance with the present invention, where a session-level attribute is used to identify the CS-specific information.

FIG. 6 is a diagram illustrating another embodiment of an SDP extension in accordance with the present invention, where a session-level attribute is used to identify the CS-specific information. In this embodiment, the CS bearer is not defined as a new media type, but rather a new session level attribute is added to inform that this session is related to a CS communication. If the recipient does not understand the attribute, it simply skips the attribute. The attribute parameters may include, for example, "x-pstn_audio," "x-pstn_video," "x-pstn_fax," and so forth. If it is relevant to differentiate between phone number formats, then other attribute names could be used such as, for example, "x-e164_audio," "x-e164_video," "x-e164_fax," and so forth.

FIG. 6 illustrates an example where a session-level attribute is used to identify the CS-specific information in accordance with one embodiment of the invention. The SDP description 600 is analogous to the SDP message portion 306 described in connection with FIG. 3, with the exception of the newly added session-level attribute 602. In this example, the attribute parameter includes an "x-pstn_audio" parameter, indicating an unregistered attribute for a CS bearer (PSTN) to carry audio communications. An associated attribute value, such as the phone number (e.g., +358501234567) of the sender of the SDP is provided.

The various SDP extension embodiments described in connection with FIGS. 3-6 are representative of the types of SDP extensions that may be utilized in accordance with the principles of the present invention. However, it should be recognized that other manners for communicating the CS-specific information using SIP through IMS may also be utilized. Thus, SDP or other session descriptions are not the only mechanism for carrying such data. For example, an entirely new data format may be defined, which would include the CS-specific information. For example, the data may be added as a new content type to the INVITE message (i.e., a new MIME type). Alternatively, the CS-specific information can be added as a new header in the SIP request. Examples of such embodiments are illustrated in FIG. 7 below.

Figure 7:
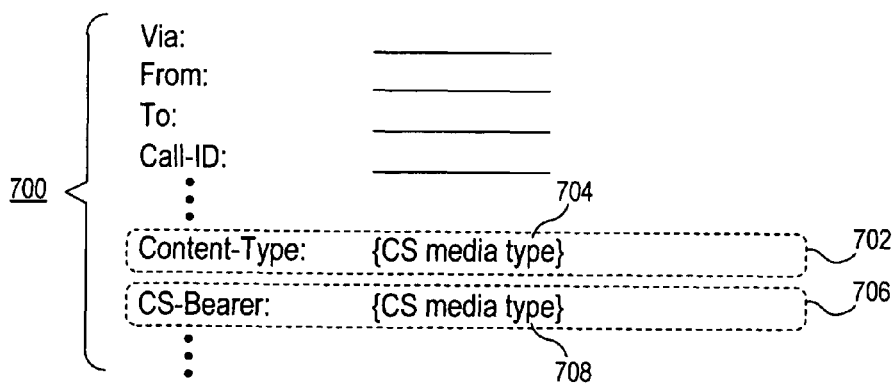
FIG. 7 is a diagram illustrating embodiments of the present invention where CS-specific information is provided as part of the SIP information.

FIG. 7 is a diagram illustrating various embodiments of the present invention, where CS-specific information is provided as part of the SIP information. FIG. 7 illustrates a representative example of a SIP message header 700. In accordance with one embodiment of the invention, CS-specific information in accordance with the present invention may be added as a new content type to a SIP message, such as a SIP INVITE request. For example, the SIP header field 702 represents a "Content-Type." As is known to those skilled in the art, the "Content-Type" is a Multipurpose Internet Mail Extensions (MIME) header field that is used in SIP headers. The purpose of a MIME Content-Type field is to describe the data contained in the body such that a receiving user agent can identify an appropriate agent or other mechanism to present the data or otherwise deal with the data in an appropriate manner.

The value associated with the Content-Type field is referred to as a media type. In accordance with one embodiment of the invention, a new CS media type 704 for the value of the Content-Type is provided, that identifies the media type as a CS bearer for communicating information via the corresponding CS domain. For example, currently existing media types include "text," "image," "audio," "video," "application," etc. In one embodiment of the invention, one or more new media types 704 for the Content-Type header field 702 are provided to identify the CS-specific information. In accordance with the invention, a media type may be defined as "cs_bearer," "pstn_audio," "pstn_video," "pstn_fax," or the like. Alternatively, a new general media type such as "cs_bearer" may be provided, having the ability to be associated with one or more subtypes. For example, current MIME text media types may be designated as a "text" media type with a "plain" subtype to identify the text as plain text. Similarly, a "cs_bearer" (or other selected media type name) may be associated with subtypes such as "pstn_audio," "pstn_video," "pstn_fax," or the like.

In another embodiment, the CS-specific information can be identified by way of a new header in the request. For example, a new header field 706 may be provided, such as a "CS-Bearer" header field. Media types 708 may be associated with such a new header field, such as "pstn_audio," "pstn_video," "pstn_fax," or the like. It should be recognized that the header fields 702, 706 represent alternative embodiments, and either one or the other may be used in a SIP header field. The header fields 702, 706 are both illustrated in the SIP message header 700 for purposes of description only.

As can be seen from the examples of FIGS. 3-7, the CS-specific information may be provided in any number of manners in accordance with the present invention. The present invention thus contemplates providing such CS-specific information in any convenient manner.

Figure 8:
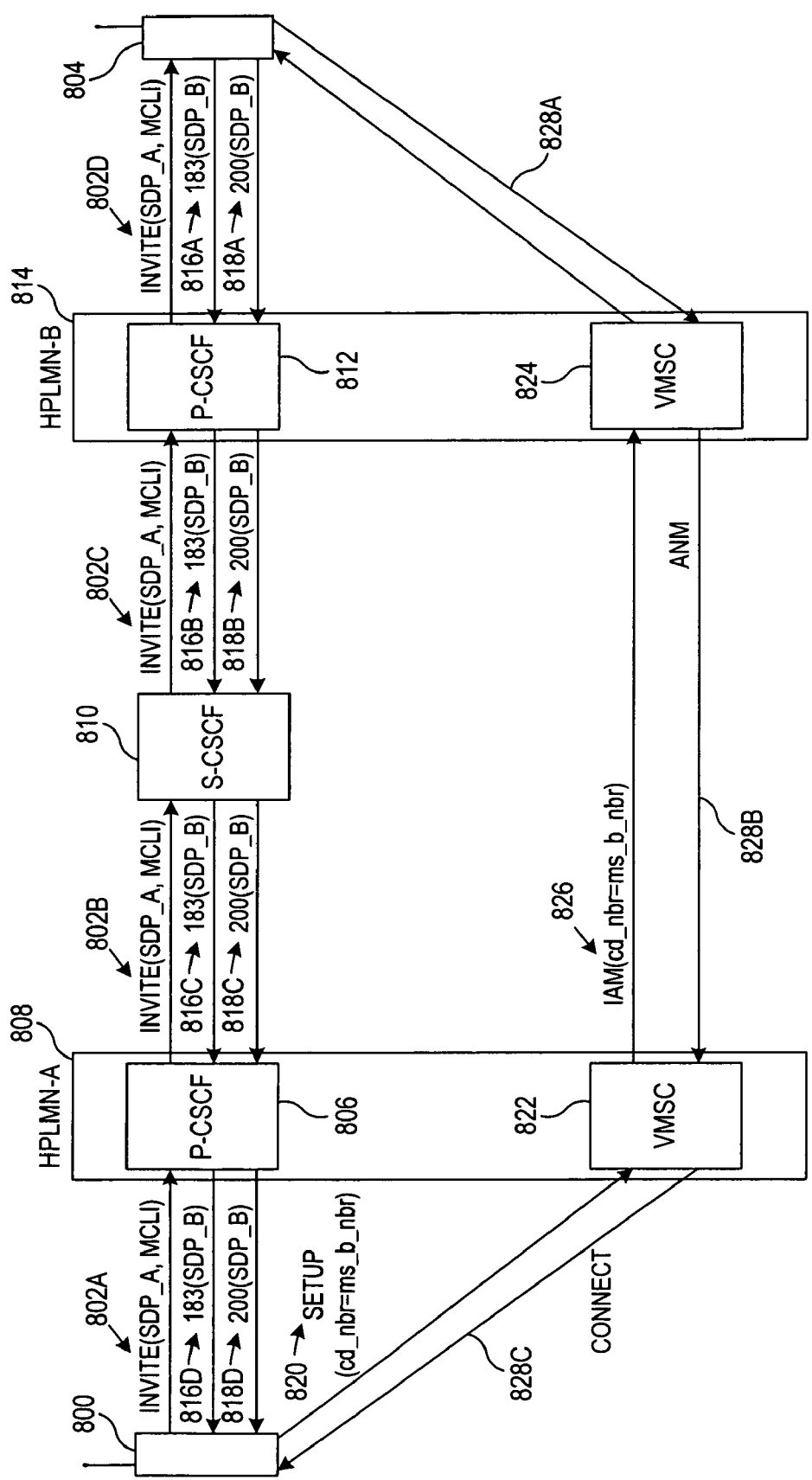
FIG. 8 is a block diagram illustrating one representative manner for providing users with IMS services while communicating via the CS domain in accordance with the present invention.

FIG. 8 is a block diagram illustrating one representative manner for providing users with IMS services while communicating via the CS domain in accordance with the present invention. The example of FIG. 8 is directed to the use of an IMS multimedia Caller Line Identification (MCLI) service in connection with a CS-domain phone communication. Generally, CLI is a service supplied by many phone providers, where the phone number is transmitted when the phone call is made. With a CLI-equipped receiving terminal, the user can see the phone number of the caller before answering the call. MCLI refers to CLI where multimedia content accompanies the phone number, or is provided in lieu of the phone number. For example, a digital picture of the caller may be transmitted, and/or an audio clip, graphics, corporate logo, and/or the like. While MCLI represents the IMS service in the illustrated example of FIG. 8, other IMS services may be provided in an analogous manner.

A first user associated with User Equipment-A (UE-A) 800 sends a SIP INVITE request 802A towards an intended call recipient, UE-B 804. In the illustrated embodiment, the INVITE request includes an SDP message (SDP-A) associated with UE-A 800. The SDP-A includes the offered medias, including the MCLI data such as text, image, business card, logo, audio clip, and/or other content. In one embodiment, the SDP-A also includes a special "CS bearer" media description line, that indicates that the bearer for audio will be allocated from the CS domain. As previously indicated, the CS-specific information may also be provided in other manners than the media description line.

The Uniform Resource Identifier (URI) of UE-B 804 is used to route the INVITE in IMS. More particularly, the INVITE 802A is received at the P-CSCF 806 in UE-A's Home Public Land Mobile Network (HPLMN-A) 808. The INVITE 802B is forwarded to the S-CSCFs 810 in the IMS, and to the P-CSCF 812 in UE-B's 804 HPLMN-B 814 as depicted by INVITE 802C. The INVITE 802D is provided to UE-B 804 from its P-CSCF 812.

UE-B 804 parses the "CS bearer" media description line (or other header, attribute, etc. carrying the CS bearer information) from the SDP-A. The SDP-A carries UE-A's 800 phone number, from which UE-B 804 now expects a phone call based on the CS bearer information. UE-B 804 also displays or otherwise presents the MCLI via UE-B 804.

UE-B 804 responds with an appropriate SIP response message 816A-816D, which is a SIP "183" response in the illustrated example. As is known in the art, a SIP "183" response indicates "session progress," which is used to convey information about the progress of the call that is not otherwise classified. Alternatively, UE-B 804 can respond with a SIP "200" (OK) message 818A-818D. In either case, the responses carry the SDP description of UE-B (i.e., SDP-B), which carries the "CS bearer" media description. Other SIP messages and responses that may occur are not shown.

UE-A 800 may initiate a call setup 820 upon receiving the 200 (OK) response 818D, or alternatively may initiate the call setup 820 in response to receiving an interim SIP response such as the 183 (session progress) response 816D. UE-A 800 initiates the call setup 820 using UE-B's 804 number (ms_b_nbr), which is continued between the VMSCs 822, 824 HPLMN-A 808 and HPLMN-B 814 via an Initial Address Message (IAM) 826. As is known in the art, an IAM is a message in the Signaling System No. 7 (SS7) or analogous circuit-switched signaling network that is used for CS call setup. The call setup continues to UE-B 804, where UE-B 804 is now expecting a CS call from UE-A 800 as a result of the SIP signaling that previously occurred. Assuming the user of UE-B 804 decides to answer the call, the CS call is then established as indicated via CS call connection path 828A, 828B, 828C.

Figure 9:
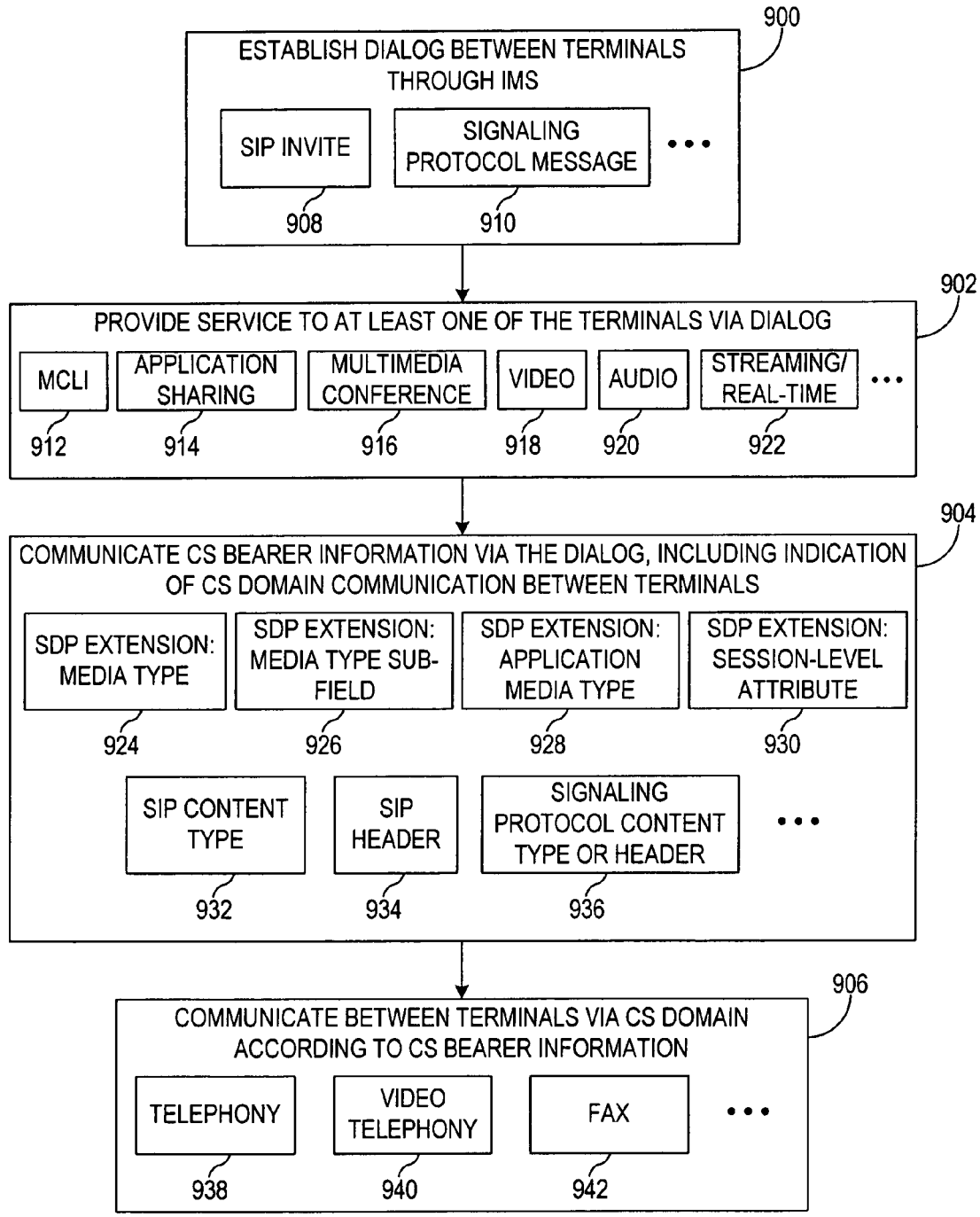
FIG. 9 is a flow diagram illustrating various embodiments of methods for providing services via a PS multimedia network to users communicating in a CS domain.

FIG. 9 is a flow diagram illustrating various embodiments of methods for providing services via a PS multimedia network to users communicating in a CS domain. The PS multimedia network may be an IMS, or other PS-based network used to facilitate communication via the Internet Protocol (IP) or other protocol that is not used to communicate information in the CS domain. A dialog is established 900 between two or more terminals through the PS multimedia network. At any point of the dialog, such as in connection with initial requests, responses, or other signaling stages of the dialog, one or more services are provided 902 to at least one of the terminals, and CS bearer information is communicated 904 via the dialog. The terminals can communicate 906 with one another via the CS domain in a manner as set forth by the CS bearer information provided via the dialog through the PS multimedia network. In this manner, terminals can communicate via the CS domain, while receiving services via the IMS or other PS multimedia network.

In accordance with one embodiment of the invention, establishing a dialog between terminals through the IMS or other PS multimedia network includes initiating the dialog using a SIP INVITE request 908 or other signaling protocol message 910. In other embodiments, providing a service(s) to one or more terminals includes providing services such as MCLI 912, application sharing 914, multimedia conference 916, video 918, audio 920, other streaming/real-time services 922, etc. In still other embodiments, communicating CS bearer information via the dialog may be performed in various manners, such as through the use of SDP extensions. Such SDP extensions include, for example, an SDP media type extension 924, SDP media type sub-field extension 926, SDP application media type extension 928, SDP session-level attribute extension 930, etc. CS bearer information may be communicated in other ways, such as via a new SIP content type 932, new SIP header 934, or other signaling protocol content type or header 936. In yet other embodiments, the CS communication between terminals may involve real-time/streaming communications, such as telephony 938, video telephony 940, facsimile transmissions 942, and the like.

Figure 10:
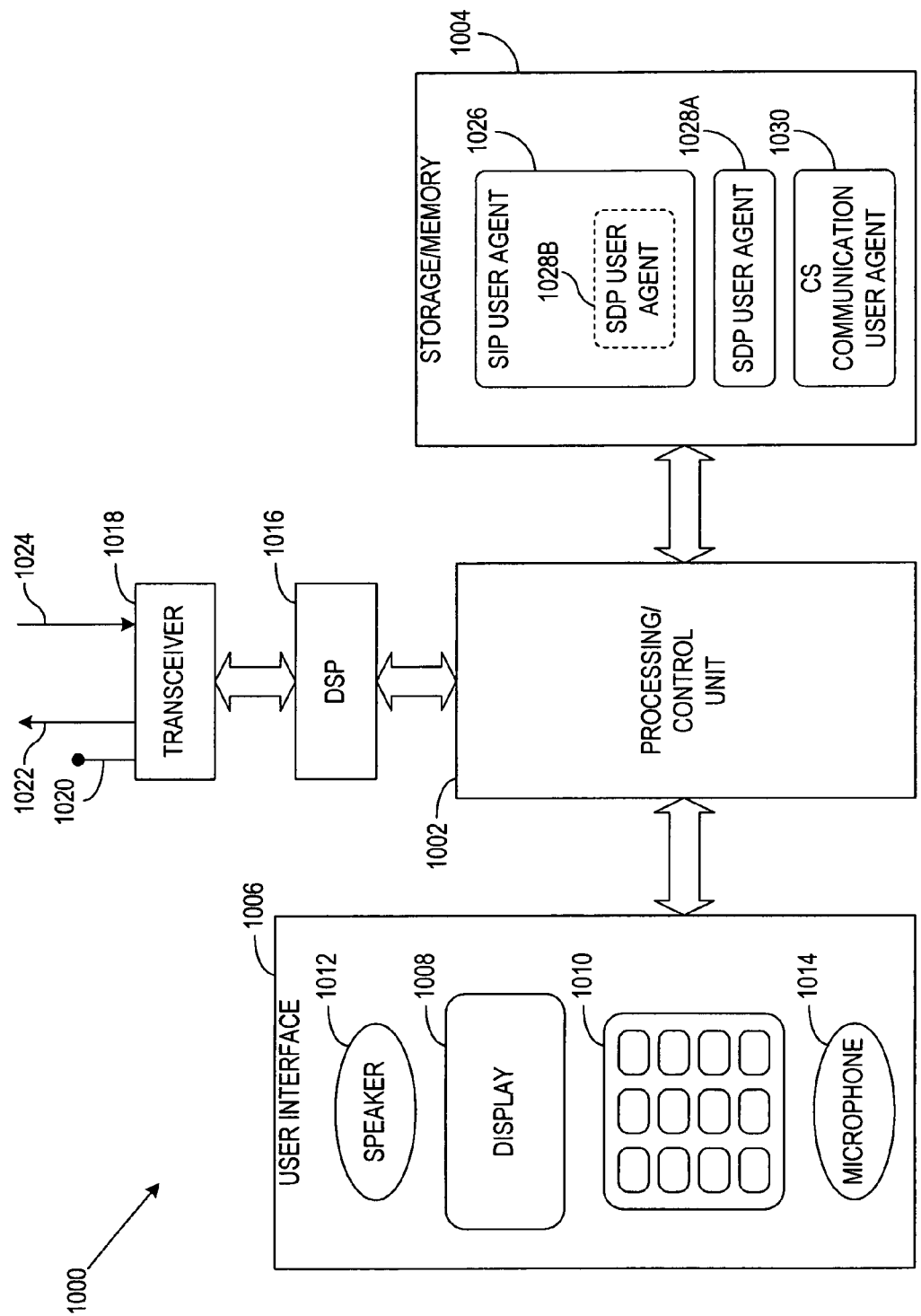
FIG. 10 illustrates a representative example of a mobile device which may serve as a UE in accordance with the present invention.

Hardware, firmware, software or a combination thereof may be used to perform the User Equipment (UE) functions and operations in accordance with the invention. The UE devices in accordance with the invention include communication devices compliant with the signaling protocol employed, such as SIP-enabled devices. These devices include, for example, mobile phones, PDAs, and other wireless communicators, as well as landline computing systems and communicators. A representative example of a mobile device which may serve as a UE in accordance with the present invention is illustrated in FIG. 10. The mobile device 1000 utilizes computing systems to control and manage the conventional device activity as well as the functionality provided by the present invention. The representative mobile device 1000 includes a computing system capable of carrying out operations in accordance with the invention. For example, the representative mobile device 1000 includes a processing/control unit 1002, such as a microprocessor, reduced instruction set computer (RISC), or other central processing module. The processing unit 1002 need not be a single device, and may include one or more processors. For example, the processing unit may include a master processor and associated slave processors coupled to communicate with the master processor.

The processing unit 1002 controls the basic functions of the mobile device 1000 as dictated by programs available in the program storage/memory 1004. The storage/memory 1004 may include an operating system and various program and data modules associated with the present invention. In one embodiment of the invention, the programs are stored in non-volatile electrically-erasable, programmable read-only memory (EEPROM), flash ROM, etc., so that the programs are not lost upon power down of the mobile device. The storage 1004 may also include one or more of other types of read-only memory (ROM) and programmable and/or erasable ROM, random access memory (RAM), subscriber interface module (SIM), wireless interface module (WIM), smart card, or other fixed or removable memory device. The relevant software for carrying out mobile device operations in accordance with the present invention may also be transmitted to the mobile device 1000 via data signals, such as being downloaded electronically via one or more networks, such as the Internet and an intermediate wireless network(s).

For performing other standard mobile device functions, the processor 1002 is also coupled to user-interface 1006 associated with the mobile device 1000. The user-interface (UI) 1006 may include, for example, a display 1008 such as a liquid crystal display, a keypad 1010, speaker 1012, and microphone 1014. These and other UI components are coupled to the processor 1002 as is known in the art. The keypad 1010 may include alpha-numeric keys for performing a variety of functions, including dialing numbers for conventional cellular/CS communication, and/or effecting SIP-based communication. Other UI mechanisms may be employed, such as voice commands, switches, touch pad/screen, graphical user interface using a pointing device, trackball, joystick, or any other user interface mechanism.

The wireless device 1000 may also include conventional circuitry for performing wireless transmissions over the mobile network. The DSP 1016 may be employed to perform a variety of functions, including analog-to-digital (A/D) conversion, digital-to-analog (D/A) conversion, speech coding/decoding, encryption/decryption, error detection and correction, bit stream translation, filtering, etc. The transceiver 1018, generally coupled to an antenna 1020, transmits the outgoing radio signals 1022 and receives the incoming radio signals 1024 associated with the mobile device 1000. For example, signals 1022, 1024 may be transmitted to a CS network or PS network via a Radio Access Network (RAN), such as provided via GSM.

In the illustrated embodiment, the storage/memory 1004 stores the various client programs such as the user agent (UA) involved in a dialog with another UE. For example, the storage 1004 includes a SIP UA 1026 or other analogous UA associated with the signaling protocol utilized. Where a new SIP Content-type or SIP header is used to transmit CS-specific information in accordance with the present invention, the SIP UA 1026 for the caller includes such information in the transmitted SIP message(s). The SIP UA 1026 at a "callee" terminal receives the SIP request, parses the message, and identifies the CS-specific information. The SIP UA 1026 also parses and processes the other SIP message information.

As previously described, other embodiments of the invention involve transmitting CS-specific information by way of a session description, such as SDP. In one embodiment of the invention, an SDP (or analogous) UA 1028A is used at the caller UE to include such information in the SDP definition. At the receiving UE, the SDP UA 1028A is used to parse the incoming SDP, identify the CS-specific information (as well as other session description information), and essentially tie together the CS session and IMS/SIP dialog in the terminal. Such an SDP UA may also be provided as part of the SIP UA 1026, as depicted by SDP UA 1028B.

The terminal also includes one or more CS communication agents 1030. For example, a CS-based telephony agent operates in connection with the processor 1002 to perform a voice call set up and to facilitate the communication between the terminal and another terminal(s). The CS communication agent 1030 may also represent other and/or additional CS-based user agents, such as a streaming video user agent, streaming audio user agent, video telephony user agent, and the like.

Analogous computing architecture is provided for landline communicators. For example, a SIP (or other) UA and SDP UA may be provided for execution by a processing system to carry out the functions in accordance with the present invention. Such a landline communicator may include a transceiver and/or other network interface to communicate information to and from the network.

The foregoing description of the exemplary embodiment of the invention has been presented for the purposes of illustration and description. It is not intended to be exhaustive or to limit the invention to the precise form disclosed. Many modifications and variations are possible in light of the above teaching. It is intended that the scope of the invention be limited not with this detailed description, but rather defined by the claims appended hereto.

What is claimed is:

1. A method comprising:
    forming a session initiation protocol (SIP) INVITE at a first user equipment (UE-A) to establish a SIP dialog associated with originating a call in the CIS domain with a second user equipment (UE-B), the SIP INVITE message including a session description protocol (PSTN) payload comprising:
    a) a connection data field indicating public switched telephony network (PSTN) connection parameters;
    b) a media type indicating an audio stream; and
    c) an indication that the circuit-switched (CS) domain will be used for delay-sensitive class flow;
    sending the SIP INVITE message via an Internet Protocol Multimedia Subsystem (IMS);

receiving a SIP response comprising a CS bearer media descriptor that includes a phone number associated with the UE-B; and sending, in response to receiving the SIP response, a circuit-switched call setup message to establish the call via the circuit switched domain, wherein the call setup message comprises the phone number associated with the UE-B.

2. The method of claim 1, wherein the session initiation protocol response comprises a session initiation protocol "183" session progress message.

3. The method of claim 1, wherein the session initiation protocol invite message is sent to the internet protocol multimedia subsystem via a proxy call state control function.

4. The method of claim 1, further comprising completing the establishment of the session initiation protocol dialog based on establishing a call with the second user equipment.

5. The method of claim 1, wherein the session initiation protocol dialog further establishes an internet protocol multimedia subsystem-specific service.

6. The method of claim 5, wherein the internet protocol multimedia subsystem-specific service comprises multimedia caller line identification.

7. The method of claim 5, wherein the internet protocol multimedia subsystem-specific service comprises an application sharing service.

8. An apparatus comprising:
a processor configured with instructions, the processor causing the apparatus to:
form a session initiation protocol (SIP) INVITE at a first user equipment (UE-S) to establish a SIP dialog associated with originating a call in the CS domain with a second user equipment (UE-B), the SIP INVITE message including a session description protocol (SDP) payload comprising:
a) a connection data field indicating public switched telephony network (PSTN) connection parameters;
b) a media type indicating an audio stream; and
c) an indication that the circuit-switched (CS) domain will be used for delay-sensitive class flow;
send the SIP INVITE message via an Internet Protocol Multimedia Subsystem (IMS);
receive a SIP response comprising a CS bearer media descriptor that includes a phone number associated with the UE-B; and
send, in response to receiving the SIP response, a circuit-switched call setup message to establish the call via the circuit switched domain, wherein the call setup message comprises the phone number associated with the UE-B.

9. The apparatus of claim 8, wherein the session initiation protocol response comprises a session initiation protocol "183" session progress message.

10. The apparatus of claim 8, wherein the session initiation protocol invite message is sent to the internet protocol multimedia subsystem via a proxy call state control function.

11. The apparatus of claim 8, wherein the processor further causes the apparatus to complete the establishment of the session initiation protocol dialog based on establishing a call with the second user equipment.

12. The apparatus of claim 8, wherein the session initiation protocol dialog further establishes an internet protocol multimedia subsystem-specific service.

13. The apparatus of claim 12, wherein the internet protocol multimedia subsystem-specific service comprises multimedia caller line identification.

14. The apparatus of claim 12, wherein the internet protocol multimedia subsystem-specific service comprises an application sharing service.

15. A non-transitory computer-readable storage medium having instructions stored thereon which are executable by a computer for performing:
forming a session initiation protocol (SIP) INVITE at a first user equipment (UE-A) to establish a SIP dialog associated with originating a call in the CS domain with a second user equipment (UE-B), the SIP INVITE message including a session description protocol (SDP)_ payload comprising:
a) a connection data field indicating public switched telephony network (PSTN) connection parameters;
b) a media type indicating an audio stream; and
c) an indication that a circuit-switched (CS) domain will be used for delay-sensitive class flow;
sending the SIP INVITE message via an Internet Protocol Multimedia Subsystem (IMS);
receiving a SIP response comprising a CS bearer media descriptor that includes a phone number associated with the UE-B; and
sending, in response to receiving the SIP response, a circuit-switched call setup message to establish the call via the circuit switched domain, wherein the call setup message comprises the phone number associated with the UE-B.

16. The non-transitory computer-readable storage medium of claim 15, wherein the instructions are further executable for completing the establishment of the session initiation protocol dialog based on establishing a call with the second user equipment.

17. The non-transitory computer-readable storage medium of claim 15, wherein the session initiation protocol dialog further establishes an internet protocol multimedia subsystem-specific service.

* * * * *

UNITED STATES PATENT AND TRADEMARK OFFICE
CERTIFICATE OF CORRECTION

| | | |
|---|---|---|
| PATENT NO. | : 8,102,839 B2 | |
| APPLICATION NO. | : 12/070873 | |
| DATED | : January 24, 2012 | |
| INVENTOR(S) | : Jarmo Kuusinen | |

It is certified that error appears in the above-identified patent and that said Letters Patent is hereby corrected as shown below:

In the Claims, Columns 18-19, lines 54-8, Claim 1 should read:

1. A method comprising:

forming a session initiation protocol invite message at a first user equipment to establish a session initiation protocol dialog associated with originating a call in a circuit-switched domain with a second user equipment, the session initiation protocol invite message including a session description protocol payload comprising:

a) a connection data field indicating public switched telephony network connection parameters;

b) a media type indicating an audio stream; and c) an indication that the circuit-switched domain will be used for delay-sensitive class flow;

sending the session initiation protocol invite message via an internet protocol multimedia subsystem;

receiving a session initiation protocol response comprising a circuit-switched bearer media descriptor that includes a phone number associated with the second user equipment; and sending, in response to receiving the session initiation protocol response, a circuit-switched call setup message to establish the call via the circuit switched domain, wherein the call setup message comprises the phone number associated with the second user equipment.

In the Claims, Column 19, lines 27-49, Claim 8 should read:

8. An apparatus comprising:

a processor configured with instructions, the processor causing the apparatus to:

form a session initiation protocol invite message at a first user equipment to establish a session initiation protocol dialog associated with originating a call in a circuit-switched domain with a second Signed and Sealed this
Fifteenth Day of May, 2012

David J. Kappos
*Director of the United States Patent and Trademark Office* user equipment, the session initiation protocol invite message including a session description protocol payload comprising:

a) a connection data field indicating public switched telephony network connection parameters;

b) a media type indicating an audio stream; and c) an indication that the circuit-switched domain will be used for delay-sensitive class flow;

send the session initiation protocol invite message via an internet protocol multimedia subsystem;

receive a session initiation protocol response comprising a circuit-switched bearer media descriptor that includes a phone number associated with the second user equipment; and send, in response to receiving the session initiation protocol response, a circuit-switched call setup message to establish the call via the circuit switched domain, wherein the call setup message comprises the phone number associated with the second user equipment.

In the Claims, Column 20, lines 17-40, Claim 15 should read:

15. A non-transitory computer-readable storage medium having instructions stored thereon which are executable by a computer for performing:

forming a session initiation protocol invite message at a first user equipment to establish a session initiation protocol dialog associated with originating a call in a circuit-switched domain with a second user equipment, the session initiation protocol invite message including a session description protocol payload comprising:

a) a connection data field indicating public switched telephony network connection parameters;

b) a media type indicating an audio stream; and c) an indication that the circuit-switched domain will be used for delay-sensitive class flow;

sending the session initiation protocol invite message via an internet protocol multimedia subsystem;

receiving a session initiation protocol response comprising a circuit-switched bearer media descriptor that includes a phone number associated with the second user equipment; and sending, in response to receiving the session initiation protocol response, a circuit-switched call setup message to establish the call via the circuit switched domain, wherein the call setup message comprises the phone number associated with the second user equipment.